United States Patent [19]

Yoshikumi et al.

[11] Patent Number: 4,957,906

[45] Date of Patent: * Sep. 18, 1990

[54] PHARMACEUTICAL COMPOSITIONS CONTAINING A DERIVATIVE OF PARA-AMINOBENZOIC ACID AS AN ACTIVE INGREDIENT

[75] Inventors: Chikao Yoshikumi, Tokyo; Yoshio Ohmura, Chiba; Fumio Hirose, Tokyo; Masanori Ikuzawa, Tokyo; Kenichi Matsunaga, Tokyo; Takayoshi Fujii, Tokyo; Minoru Ohhara, Tokyo; Takao Ando, Tokyo, all of Japan

[73] Assignee: Kureha Kagaku Kogyo Kabushiki Kaisha, Tokyo, Japan

[*] Notice: The portion of the term of this patent subsequent to Apr. 19, 2000 has been disclaimed.

[21] Appl. No.: 163,204

[22] Filed: Feb. 26, 1988

Related U.S. Application Data

[60] Continuation of Ser. No. 879,508, Jun. 27, 1986, abandoned, which is a continuation of Ser. No. 686,415, Dec. 26, 1984, abandoned, which is a continuation of Ser. No. 352,858, Feb. 26, 1982, Pat. No. 4,569,842, which is a division of Ser. No. 81,190, Oct. 2, 1979, Pat. No. 4,322,408.

[30] Foreign Application Priority Data

| Apr. 11, 1978 | [JP] | Japan | 53-42576 |
| May 26, 1978 | [JP] | Japan | 53-63146 |
| Dec. 29, 1978 | [JP] | Japan | 53-161385 |
| Dec. 29, 1978 | [JP] | Japan | 53-161386 |

[51] Int. Cl.$^5$ .................................... A61K 31/70
[52] U.S. Cl. .................................... 514/42; 536/22
[58] Field of Search .................. 536/22, 23; 514/25, 514/42

[56] References Cited

U.S. PATENT DOCUMENTS

| 4,313,939 | 2/1982 | Yoshikumi et al. |
| 4,315,921 | 2/1982 | Yoshikumi et al. |
| 4,322,408 | 3/1982 | Yoshikumi et al. |
| 4,322,409 | 3/1982 | Yoshikumi et al. |
| 4,380,536 | 4/1983 | Yoshikumi et al. |
| 4,409,240 | 11/1983 | Takita et al. |
| 4,440,757 | 4/1984 | Yoshikumi et al. |
| 4,450,156 | 5/1984 | Yoshikumi et al. |
| 4,555,505 | 11/1985 | Yoshikumi et al. |
| 4,559,327 | 12/1985 | Yoshikumi et al. |
| 4,569,842 | 2/1986 | Yoshikumi et al. |
| 4,596,794 | 6/1986 | Yoshikumi et al. |
| 4,637,998 | 1/1987 | Yoshikumi et al. |
| 4,649,133 | 3/1987 | Yoshikumi et al. |
| 4,657,895 | 4/1987 | Yoshikumi et al. |
| 4,663,312 | 5/1987 | Yoshikumi et al. |
| 4,673,669 | 6/1987 | Yoshikumi et al. |
| 4,708,950 | 11/1987 | Yoshikumi et al. |
| 4,748,159 | 5/1988 | Yoshikumi et al. |

OTHER PUBLICATIONS

Bonadonna et al., Combination Chemotherapy as an Adjuvant Treatment in Operable Breast Cancer, New England Journal of Medicine, vol. 294, 405-410.

Fisher et al., 1-Phenylalanine Mustard (L-PAM) in the Management of Primary Breast Cancer, New England Journal of Medicine, vol. 292, 117-122.

Primary Examiner—Blondel Hazel
Attorney, Agent, or Firm—Wegner & Bretschneider

[57] ABSTRACT

Disclosed is a pharmaceutical composition containing an aminobenzoic acid derivative as an active ingredient represented by the following general formula:

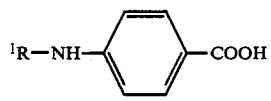

wherein $^1R$ denotes one member selected from the group consisting of the residual groups formed by removing OH at 1(alpha) or 1(beta) position from arabinose, glucose, galactose and mannose, or a pharmaceutically acceptable salt thereof.

7 Claims, No Drawings

PHARMACEUTICAL COMPOSITIONS CONTAINING A DERIVATIVE OF PARA-AMINOBENZOIC ACID AS AN ACTIVE INGREDIENT

This application is a continuation of Ser. No. 879,508 filed June 27, 1986, now abandoned, which is a continuation of Ser. No. 686,415 filed Dec. 26, 1984, now abandoned, which is a continuation of Ser. No. 352,858 filed Feb. 26, 1982, now U.S. Pat. No. 4,569,842, which is a division of Ser. No. 081,190 filed Oct. 2, 1979, now U.S. Pat. No. 4,322,408 which is continuation-in-part Ser. No. 024,095 filed Mar. 26, 1979 now abandoned.

BACKGROUND OF THE INVENTION

The present invention relates to a pharmaceutical composition having a blood sugar reducing activity, a blood pressure reducing activity, a blood lipid reducing activity, an anti-inflammatory activity, a central nerve suppressing activity and an antitumor activity and containing an aminobenzoic acid derivative as an active ingredient represented by the following general formula:

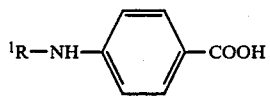
(1)

wherein $^1R$ denotes one member selected from the group consisting of the residual groups formed by removing OH at 1 (alpha) or 1(beta) position from arabinose, glucose, galactose and mannose, or a pharmaceutically acceptable salt thereof.

The inventors of the present invention, during the course of searching chemical compounds having antitumor activity, have found that chemical compounds represented by the abovementioned formula (1) have respectively a number of physiological activities such as blood sugar- reducing activity, antihypertensive activity, blood lipid-reducing activity, antiinflammatory activity and central nerve-depressing activity in addition to its antitumor activity.

Although the above-mentioned aminobenzoic acid derivatives are known compounds, no report has been found on the physiological activity of the compounds.

Inoue, et al. "N-glycosides. XVIII. Synthesis of the N-glycosides of p-aminobenzoic acid and its ethyl ester." Chemical Abstracts, Vol 48 (1954) Column 2001 c., Inoue, et al. "N-glycosides. XXV. The paper chromatography of N-glycosides", Chemical Abstracts, Vol 48 (1954) Column 2003 a. and Inoue, et al. "N-glycosides. XXVI. The formation of aromatic N-glycosides under mild conditions." Chemical Abstracts, Vol 48 (1954) Column 2003 e. disclose the chemical syntheses of N-glycosides of p-aminobenzoic acid and their esters. However, there is no utility disclosed in this prior arts and no teaching of pharmaceutical "dosage unit forms".

Furthermore, although U.S. Pat. No. 2,659,689 discloses a p-aldimino benzoic ester and a composition for protecting the human skin from erythema producing rals, the composition comprising a solution of p-aldimino benzoic ester, there is no teaching of pharmaceutical "dosage unit forms".

Accordingly, the present invention has the object of providing a pharmaceutical composition having effectiveness in antitumour activity, blood sugar-reducing activity, antihypertensive activity, blood lipid-reducing activity, antiinflammatory activity and central nerve-depressing activity, based on the discovery of the new medical use of the chemical compounds represented by the above-mentioned formula (1).

The present invention will be explained in detail in the followings.

BRIEF DESCRIPTION OF THE DRAWING

The annexed FIGS. 1-8 show respectively the infrared absorption spectra of respective compounds No. 1 No. 8 in Table 1.

DETAILED DESCRIPTION OF THE INVENTION

The active ingredient of the pharmaceutical composition of the present invention is a compound represented by the following formula:

wherein $^1R$ is as described above, or its pharmaceutically acceptable salt selected from the group consisting of its Na-, K-, ½Mg-, ½Ca- and ⅓Al- salts. The sugar moiety of the active ingredient has a structure of six membered heterocyclic ring.

The method of preparation of the active ingredient of the present invention is illustrated as follows:

A mixture of 4.5 to 5 g of p-aminobenzoic acid, 5–6 g of a mono saccharide (L-arabinose, D-xylose, D-glucose, D-galactose, L-rhamnose or D-mannose) and 0.1 to 0.5 g of ammonium chloride (formic acid, hydrochloric acid, acetic acid, or magnesium chloride) was heated in 40 to 90 ml of 95 to 100% ethanol or pure methanol under a reflux condenser to induce condensation. After the reaction is over, the reactant is left at room temperature or in a cool place and the crystals separated out are collected by filtering the reactant solution. These crystals are washed with water, ethanol or ethyl ether, and then recrystallized from methanol, ethanol or an aqueous solution of methanol or ethanol.

In order to substitute the hydrogen atom of the carboxyl group of the thus prepared compound with a base, it is preferable to follow the known method. The compound, paraaminobenzoic acid —N— pyranoside, is dissolved in an aqueous ethanolic solution and an inorganic salt is added to the solution to effect the substitution.

The physical properties of the compounds (the active ingredient of the pharmaceutical composition of the present invention) prepared by the above-mentioned methods are shown in Table 1, and their infrared absorption spectra are respectively shown in FIGS. 1 to 13. Methods of determination of the physical properties are as follows:

TABLE 1
Physical Properties of the Active Ingredients

| Compound | Melting point (°C.) | Specific rotation $(\alpha)_D^{20}$ | Elementary analysis (%) C:H:N | Ultraviolet absorption Maximum (millimicron) |
|---|---|---|---|---|
| 1. p-Aminobenzoic acid-N-L-arabinoside | 156–158 | −4 in 95% ethanol | 53.3:5.7:5.2 (53.5:5.6:5.2)* | 29 |
| 2. Sodium p-aminobenzoate-N-L-arabinoside | 163–173 (decomp.) | −41 in water | 50.0:4.2:4.7 (49.8:4.2:4.8) | 274 |
| 3. p-Aminobenzoic acid-N-D-glucoside | 132 (decomp.) | −68.6 in 94% ethanol | 49.5:5.8:4.6 (49.2:6.0:4.4) | 288 |
| 4. Sodium p-aminobenzoate-N-D-glucoside | 145–160 | −55 in water | 45.8:5.2:4.3 (46.0:5.3:4.1) | 274 |
| 5. p-Aminobenzoic acid-N-D-galactoside | 154–156 | −110 (16° C.) in 94% ethanol | 49.0:6.3:4.5 (49.2:6.0:4.4) | 289 |
| 6. Sodium p-aminobenzoate-N-D-galactoside | 150–162 | +10 in water | 46.0:5.6:4.1 (46.0:5.3:4.1) | 275 |
| 7. p-Aminobenzoic acid-N-D-mannoside | 182 (decomp.) | +35.7 in 94% ethanol | 52.0:5.7:4.7 (52.5:5.7:4.7) | 290 |
| 8. Sodium p-aminobenzoate-N-D-mannoside | 185–196 (decomp.) | −2 in water | 46.1:5.5:4.0 (46.0:5.3:4.1) | 274 |

Note:
( : : ) : theoretical values of C, H and N (%).

(1) Melting point: determined by the use of micro melting point determination apparatus made by Yanagimoto Works, Japan.

(2) Specific rotation: determined by using direct reading polarimeter Model OR-50 made by Yanagimoto Works, Japan, with a thickness of 50 mm of an aqueous ethanolic solution of the acidic active ingredient and an aqueous solution of the sodium salt of the acidic active ingredient.

(3) Molecular composition: Elementary analysis was carried out by using OHN-Coder Model MT-2 made by Yanagimoto Works, Japan.

(4) Ultraviolet absorption spectrum: by using self-recording spectrophotometer Model PS-3T made by Hitachi Works, Japan, on an aqueous ethanolic solution of the acidic active ingredient and on an aqueous solution of the sodium salt of the acidic active ingredient of the medicine, (5) Infrared absorption spectrum: determined by KBr-method using infrared absorption spectrometer Model DS-701G made by Nippon Bunko Co., Ltd., Japan. The chart number of the spectrogram coincides with the number of specimens of the active ingredient of the pharmaceutical composition.

The followings are the physiological properties of the active ingredient of the pharmaceutical composition of the present invention described in the order of (1) acute toxicity, (2) antimicrobial activity, (3) mutagenicity, (4) delayed-type intracutaneous reaction and (5) antibody-producing activity.

(1) Acute toxicity

Acute toxicity of the active ingredient was examined by respective intraperitoneal and oral (forcible) administration to ICR-JCL mice. The specimen was dissolved in the physiological saline solution in intraperitoneal administration, and dissolved in distilled water in oral administration.

Their symptoms were observed after administration until the 7th day of administration, and LD$_{50}$ of the specimen was obtained from the mortality accumulated to the 7th day, according to the graphic method of Litchfield-Wilcoxon. The results are shown in Table 2. As is seen in Table 2, all of the active ingredients are qualified to be highly safe active ingredients of the pharmaceutical composition.

TABLE 2
Acute toxicity of the active ingredients (LD$_{50}$ in g/kg)

| Compound | Route of intraperitoneal | administration oral |
|---|---|---|
| Sodium p-aminobenzoate-N-L-arabinoside | 10.22 | 10.80 |
| Sodium p-aminobenzoate-N-D-glucoside | >15.00 | >15.00 |
| Sodium p-aminobenzoate-N-D-galactoside | 12.0 | 14.55 |
| Sodium p-aminobenzoate-N-D-mannoside | >10.00 | >10.00 |

Antimicrobial activity

The active ingredient was dissolved in distilled water at a series of two fold dilution system. These diluted solutions were mixed with agar medium in 9 times by volume, and the mixture was poured into a petri dish. Heart infusion agar medium was used for bacteria, and Sabouraud's agar medium was used for fungi. After streaking with the pre-culture, the inoculated plates were incubated at 37° C. for 20 to 24 hours for bacteria and at 25° C. for 3 to 7 days for fungi, and then the growth was examined. The following microorganisms were used for assessing the antimicrobial activity:

*Pseudomonas aeruginosa* IAM 1514
*Escherchia coli* IFO 12734
*Staphylococcus aureus* 209 P
*Bacillus subtilis* IMM 1069
*Saccharomyces cerevisiae* IAM 4207
*Candida albicans* ATCC 752
*Trichophyton mentagrophytes* IFO 6124
*Aspergillus niger* IAM 3001

As the result of the above-mentioned tests, it was found that none of the tested active ingredients showed growth inhibition of all the microorganisms at a concentration of 1 mg/ml.

(3) Mutagenicity

As the first stage, the active ingredients were tested by recession assay (i), and as the second stage, they were tested by reversion assay (ii).

(i) A strain of *Bacillus subtilis* M 45, a defectant of recombination repair, and another strain of *Bacillus subtilis* H 17 keeping recombination repair activity were inoculated to make thin own streaks not crossed at the start on B-2 agar culture plate (made by dissolving 10 g of meat extract, 10 g of polypeptone, 5 g of sodium chloride and 15 g of agar in 1000 ml of distilled water at a pH of 7.0).

Then, a circular sheet of filter paper 8 mm in diameter, which absorbed 0.04 ml of an aqueous solution of the active ingredient (using sterilized water) was put on the surface of the agar plate so as to cover the starting point of the above-mentioned streaks of bacterial culture. The inoculated B-2 agar culture was kept at 37° C. for a night and the length of growth-inhibited region was measured. Kanamycin was used as the negative control and Mitomycin C was used as the positive control. The results of the fec-assay are shown in Table 3.

(ii) The strains TA 98 and TA 100 (both are histidine requiring) of Salmonella typhimurium were used in the reversion assay.

Into 2 ml of a soft agar culture medium (the medium itself contains 6 g of sodium chloride and 6 g of agar in 1000 ml of distilled water) to which one tenth by volume of an aqueous solution of 0.5 mM of biotin and 0.5 mM of histidine, 0.1 ml of the bacterial suspension and 0.1 ml of an aqueous solution of the active ingredient were admixed and the mixture was layered on the minimum agar culture medium. After 2 days of incubation at 37° C., the number of revertant colonies was counted. Furylfuramide (AF-2) was used as the positive control. The results of the reversion assay are shown in Table 4.

As is seen in Table 3, the active ingredients showed no mutagenicity even at a high concentration of 5000 microgram/disk. And as is seen in Table 4, the rate of occurrence of mutation by the active ingredient of the pharmaceutical composition of the present invention, did not show any difference from that in the control to which no substance was added, even at a high concentration of 5000 microgram/plate. These findings demonstrate that the active ingredient is safe in view of mutagenicity.

TABLE 3

| | Result of rec-assay | | | |
|---|---|---|---|---|
| | | Length of growth-inhibition zone | | |
| Compound | Concentration (μg/plate) | M 45 (mm) | H 17 (mm) | *difference (mm) |
| Sodium p-aminobenzoate-N-L-arabinoside | 500 | 0 | 0 | 0 |
| | 5000 | 0 | 0 | 0 |
| Sodium p-aminobenzoate-N-D-glucoside | 500 | 0 | 0 | 0 |
| | 5000 | 0 | 0 | 0 |
| Sodium p-aminobenzoate-N-D-galactoside | 500 | 0 | 0 | 0 |
| | 5000 | 0 | 0 | 0 |
| Sodium p-aminobenzoate-N-D-mannoside | 500 | 0 | 0 | 0 |
| | 5000 | 0 | 0 | 0 |
| Kanamycin | 10 | 5 | 4 | 1 |
| Mitomycin C | 0.05 | 12 | 2 | 10 |

Note:
*difference = length of inhibition zone of M 45 minus length of inhibition zone of H 17

TABLE 4

| | Results of Reversion assay Test | | |
|---|---|---|---|
| | Concentration | Number of revertant colonies (n/plate) | |
| Compound | (μg/plate) | TA 100 | TA 98 |
| Sodium p-aminobenzoate-N-L-arabinoside | 5000 | 51 | 3 |
| Sodium p-aminobenzoate-N-D-glucoside | 5000 | 104 | 11 |
| Sodium p-aminobenzoate-N-D-galactoside | 5000 | 51 | 7 |
| Sodium p-aminobenzoate-N-D-mannoside | 5000 | 138 | 5 |
| Furylfuramide | 0.1 | 911 | 167 |
| Control (nothing added) | — | 149 | 13 |

(4) Delayed-type intracutaneous reaction

In order to know the effects of the active ingredients on cellular immunity, the foot pad reaction test was carried out using ICR-JCL mice as experimental animals and erythrocytes of sheep as an antigen.

A mouse was primary-sensitized by injecting 0.2 ml of 10% suspension of sheep erythrocytes in physiological saline solution from the caudal vein and after 7 days of the first sensitization, 0.05 ml of 40% suspension of sheep's erythrocytes in physiological saline solution was injected in the foot pad for the second sensitization. The thickness of the foot pad was determined on the next day. The administration of the active ingredient of the pharmaceutical composition of the present invention was carried out at the dosage of 250 mg/kg/day once a day for consecutive 5 days centering around the day when the first sensitization was carried out.

As the result, the increment of the thickness of the foot pad of the mouse administered with the active ingredient showed no significant difference as compared to the increment in the group of mouse not administered with the active ingredient.

(5) Antibody producing activity

In order to know the effects of the active ingredients on humoral immunity, the hemagglutination test was carried out using ICR-JCL mice sensitized with sheep erythrocytes.

A mouse was sensitized by injecting 0.2 ml of 10%. suspension of sheep erythrocytes in physiological saline solution from the caudal vein and after 7 days of sensitization the mouse blood was sampled for the hemagglutination test of determination of the antibody-producing activity. The active ingredient was administered for consecutive 5 days centering around the day of sensitization, intraperitoneally at the dosage of 250 mg/kg/day.

As the result, there was no significant difference in agglutination titer between the group administered with the active ingredient and the control group.

The followings are the pharmacological properties of the active ingredients of the pharmaceutical composition of the present invention described in the order of (1) blood sugar-reducing activity, (2) antihypertensive activity, (3) antitumour activity, (4) analgetic activity, (5) antipyretic activity, (6) antiinflammatory activity, and (7) blood lipid reducing activity.

(1) Blood sugar reducing activity

Streptozotocin was administered intraperitoneally to a group of Wistar rats at a dosage of 60 mg/kg and after confirming the positivity of urinary sugar of the animals on the 8th day, regular insulin was further administered to the rats to reduce both the urinary sugar and the blood sugar. Out of thus treated animals, those which certainly showed a higher urinary sugar value and also a higher blood sugar value (mean value of 500 mg/dl) after a few days of insulin-administration were used as the model animals suffering from artificial diabetes mellitus. The active ingredient was administered to the model animals orally as a solution in distilled water at the respective dosages of 30 and 300 mg/kg. Blood specimens were collected after 3 and 6 hours of the administration, and the determination of glucose in the specimen was carried out by using a RaBA kit (made by Chugai Pharmaceutical Co., Japan) according to the enzyme method.

The results are shown in Table 5. As is seen in Table 5, the difference between the values of blood sugar before and after the administration of every active ingredient ($\Delta$ value) was larger than the $\Delta$ value of control which were given only distilled water.

TABLE 5

Blood sugar-reducing activity

| Compound | Dose (mg/kg) | Change ($\Delta$ value, mg/dl) of blood sugar after | |
|---|---|---|---|
| | | 3 hr. | 6 hr. |
| Sodium p-aminobenzoate-N-L-arabinoside | 30 | −88 | −181 |
| | 300 | −108 | −82 |
| Sodium p-aminobenzoate-N-D-glucoside | 30 | −68 | −45 |
| | 300 | −80 | −50 |
| Sodium p-aminobenzoate-N-D-galactoside | 30 | −76 | −62 |
| | 300 | −91 | −45 |
| Sodium p-aminobenzoate-N-D-mannoside | 30 | −160 | −118 |
| | 300 | −190 | −146 |
| Control | — | −36 | −39 |

(2) Antihypertensive activity

An aqueous solution of the active ingredient in distilled water was orally administered to rats of spontaneous hypertension at respective dosages of 30 and 300 mg/kg and their blood, pressure was determined after 3 and 6 hours of administration by a sphygmomanometer (made by Ueda Works, Japan, Model USM105R). The difference of blood pressures before and after the administration was used to evaluate the antihypertensive activity of the active ingredients. Mean value of blood pressure of the above-mentioned rats in spontaneous hypertension was 200 mmHg.

The results are shown in Table 6. As is seen in Table 6, all the tested active ingredients clearly showed the antihypertensive effect.

TABLE 6

Antihypertensive Activity

| Compound | Dose rate (mg/kg) | Reduced amount of blood pressure after | |
|---|---|---|---|
| | | 3 hr. | 6 hr. |
| | | (mm Hg) | |
| Sodium p-aminobenzoate-N-L-arabinoside | 30 | 8 | 6 |
| | 300 | 14 | 12 |
| Sodium p-aminobenzoate-N-D-glucoside | 30 | 23 | 23 |
| | 300 | 18 | 20 |
| Sodium p-aminobenzoate-N-D-galactoside | 30 | 6 | 8 |
| | 300 | 13 | 14 |
| Sodium p-aminobenzoate-N-D-mannoside | 30 | 16 | 20 |
| | 300 | 18 | 22 |
| Control | — | −2* | 2 |

Note:
*Blood pressure was raised by 2 mmHg.

(3) Antitumour activity

Sarcoma 180 were transplanted subcutaneously into the right axillary of ICR-JCL mice at the rate of $1 \times 10^6$ cells/mouse, and from after 24 hours of transplantation an aqueous solution of the active ingredient in sterilized physiological saline solution was orally administered every other day at a dose rate of 500 mg/kg, 10 times in all. On the 25th day of the transplantation, the nodular tumour(s) was extirpated and weighed.

The inhibition ratio (I.R.) (%) of the active ingredient was calculated by the following formula:

$$(1 - T/C) \times 100 = I.R. (\%)$$

wherein

T: mean weight of the tumour(s) in treated group of mice

C: mean weight of the tumour(s) in control group* of mice

Note: *mice transplanted, but not administered.

The results of the test are shown in Table 7. As is seen in Table 7, all the active ingredients tested exhibited an antitumour activity.

TABLE 7

Antitumourigenic activity against Sarcoma-180

| Compound | Inhibition ratio (I.R. %) |
|---|---|
| Sodium p-aminobenzoate-N-L-arabinoside | 52.7 |
| Sodium p-aminobenzoate-N-D-glucoside | 15.9 |
| Sodium p aminobenzoate-N-D-galactoside | 44.1 |
| Sodium p-aminobenzoate-N-D-mannoside | 29.0 |

Note: Amount of administration was 10 × 500 mg/kg p.o.

(4) Analgetic Activity

Determination by the mechanical stimulation method (by applying pressure)

Female ICR mice which showed a threshold value of pain of 50 to 80 mmHg when their tail base part was pressed by a pressure stimulation apparatus (made by Natsume Works, Japan) of Takagi and Kameyama were chosen as test animals, ten animals comprising a group.

After administering the active ingredient, the test was carried out as the time passes and the applied pressure and the time period until the animal showed a quasi-escaping reaction were determined to evaluate the analgetic activity of the active ingredient.

The results are shown in Table 8. As is seen in Table 8, the pressure applied on animals when the animal showed the quasi-escaping reaction was higher in animals to which the active ingredient had been applied than in animals not administered, and the time period from the beginning to the time point when the animal showed the reaction was longer in animals administered with the active ingredient than in animals not administered. Thus, the analgetic activity of the active ingredient was confirmed, Determination by the chemical stimulation method The active ingredient was orally administered to a group (ten animals) of female ICR mice of age of 5 to 6 weeks, and after 30 min of the administration an aqueous 0.6% acetic acid solution was intraperitoneally injected into the mouse at a dose rate of 0.1 ml/10 g of body weight. The number of writhing motion which occurred in the mouse during 10 minutes after 10 minutes of intraperitoneal administration was recorded. The analgetic activity was evaluated from the writhing syndrome inhibiting ratio obtained by the following formula:

$(1-T/C) \times 100$ = writhing syndrome inhibiting ratio (%)

wherein
T: mean number of writhing syndrome in the group administered
C: mean number of writhing syndrome in the control group.

The results are shown in Table 9. As is seen in Table 9, every active ingredient of the pharmaceutical composition of the present invention showed analgetic activity. The above-mentioned process was carried out following the method of Kostet et al. (1959)

TABLE 8

| Analgetic activity by the mechanical stimulation method | | |
|---|---|---|
| | Quasi-escope reaction pressure at time until | |
| Compound | (mmHg) occurrence | (sec.) |
| Sodium p-aminobenzoate-N-L-arabinoside | 102 | 47 |
| Sodium p-aminobenzoate-N-D-glucoside | 89 | 41 |
| Sodium p-aminobenzoate-N-D-galactoside | 76 | 40 |
| Sodium p-aminobenzoate-N-D-mannoside | 95 | 39 |
| Control | 70 | 33 |

Note: Amount of administration, 1000 mg/kg p.o.

TABLE 9

| Analgetic activity by the chemical stimulation method | |
|---|---|
| Compound | I.R. (%) |
| Sodium p-aminobenzoate-N-L-arabinoside | 45.7 |
| Sodium p-aminobenzoate-N-D-glucoside | 16.8 |
| Sodium p-aminobenzoate-N-D-galactoside | 33.2 |
| Sodium p-aminobenzoate-N-D-mannoside | 71.2 |

Note: Amount of administration was 1000 mg/kg p.o.

(5) Antipyretic activity

Following the method of Winter et al. (1961), a 20% suspension of beer yeast was subcutaneously injected to a group (consisting of 6 animals) of rats, and after 10 hours of fasting, the active ingredient was orally administered to the rats and their rectal temperature was determined.

The antipyretic activity is expressed by the ratio of inhibiting pyrexia due to beer yeast (I.R. %) at the time when the antipyretic activity of the active ingredient is at its maximum according to the following formula:

$$\text{Antipyretic activity} = \text{I.R. (\%)} = \frac{C_1 - T}{C_1 - C_2} \times 100$$

wherein
T: mean rectal temperature of rats to which the active ingredient was administered.
$C_1$: mean rectal temperature of rats injected beer yeast, without the active ingredient.
$C_2$: mean rectal temperature of untreated rats (control)

The results are shown in Table 10. As is seen in Table 10, all the active ingredients exhibited a considerable antipyretic activity.

TABLE 10

| Antipyretic activity | |
|---|---|
| Compound | Antipyretic activity (suppressing pyrexia) I.R.(%) |
| Sodium p-aminobenzoate-N-L-arabinoside | 88.2 |
| Sodium p-aminobenzoate-N-D-glucoside | 58.1 |
| Sodium p-aminobenzoate-N-D-galactoside | 65.5 |
| Sodium p-aminobenzoate-N-D-mannoside | 20.5 |

(6) Antiinflammatory activity (a) Carrageenin-edema inhibitory activity

Following the method of Van Arman et al. (1963), the active ingredient was forcibly and orally administered to each rat of a group consisting of 10 animals at the dose rate of 1000 mg/kg, and after one hour of the administration 0.1 ml of 1% suspension of carrageenin in physiological saline solution was injected to their right foot pad. The volume of the foot pad was determined as time passes and the antiinflammatory activity was expressed by the ratio of inhibition of the swelling of the foot pad due to carrageenin by the active ingredient, using the maximum determined value during 1 to 4 hours after the injection, and calculating by the following formula:

$(1-T/C) \times 100 = \text{I.R.}(\%) = $ antiinflammatory activity wherein
T: mean value of volumes of planta in administered animals
C: mean value of volume of the foot pad of control (not administered and then injected)

The results are shown in Table 11. As is seen in Table against the edema caused by carrageenin.

(b) Antigranuloma activity

Following the method of Winter et al. (1963), two cotton wool pellets were implanted into the skin of back of each rat of a group consisting of 6 rats at the symmetrical positions having the median line as the axis of symmetry, the weight of one pellet being 30±1 mg. Oral administration of 1000 mg/kg/day of the active ingredient was carried out for consecutive 7 days. On the 8th day, the granuloma formed in the rats was extirpated and weighed after drying. The antigranuloma activity expressed by the ratio of inhibition of the growth of the granuloma (I.R., %) was calculated in a manner as shown in (6)(a), and the results are shown in Table 11. As is seen in Table 11, each active ingredient exhibited the inhibiting activity of growth of the granuloma.

(c) Antiexudation activity

Following the method of Baris et al. (1965), a volume of air was injected subcutaneously in the back of each rat of a group consisting of 6 rats to make a air pouch, and then 0.5 ml of 1% croton oil solution is sesame oil was injected into the pouch. The oral administration of 1000 mg/kg/day of the active ingredient was then began to continue for 5 days. On the 6th day, the amount of exsudated liquid into the pouch was determined and the anti exsudation activity expressed by the ratio of inhibitory activity to exudation was calculated in a manner as shown in (6)(a). The results are shown in Table 11. As is seen in Table 11, all the active ingredient tested exhibited the anti-exsudation activity.

(d) Antiadjuvant-arthritis activity

Following the method of Fujiwara et al. (1971), *Mycrobacterium tuberculosis* suspended in liquid paraffin was injected subcutaneously into the right foot pad of each rat of a group consisting of 6 rats. After 14 days -of the injection, rats with similar volume of the foot pad were chosen to form groups (10 animals/group), each active ingredient was orally administered daily from the 15th day for consecutive 7 days at the dose rate of 1000 mg/kg/day. The volume of the foot pad of rats was determined, and the antiadjuvant arthritis activity of each active ingredient was calculated as the ratio of inhibiting the swelling of the foot pad by using the formula shown in (6)(a). The results are shown in Table 11. As is seen in Table 11, all the tested active ingredient exhibited the antiadjuvant arthritis activity, especially sodium p-aminobenzoate-N-L-arabinoside giving a conspicuous activity of I.R. of 35.2%.

TABLE 11

| | Antiinflammatory activity | | | |
|---|---|---|---|---|
| Compound | *edema | *granuloma | *exudation | *arthritis |
| Sodium p-aminobenzoate-N-L-arabinoside | 38.3 | 14.9 | 25.2 | 35.2 |
| Sodium p-aminobenzoate-N-D-galactoside | 10.0 | 5.1 | 13.2 | 15.6 |
| Sodium p-aminobencoate-N-D-glucoside | 5.9 | 18.6 | 6.2 | 20.5 |
| Sodium p-aminobencoate-N-D-mannoside | 3.8 | 29.9 | 5.0 | 30.5 |

Note:
Amount of adminstration of the active ingredient = 1000 mg/kg/day (7) Blood lipid reducing activity Japanese male white rabbits were fed for about 3 months with solid feed (CR-1) containing 1% of cholesterol and those animals in which the increase of seral lipid component was confirmed were used as the model animals having experimental arteriosclerosis.

An aqueous solution of the active ingredient in distilled water was administered respectively at the dose rates of 30 and 300 mg/kg orally and after the administration, blood specimen was collected as time passes from the auricular vein and the change of total cholesterol (determined by the enzyme method), phospholipid (determined by the enzyme method) and beta-lipoprotein (determined by turbidmetry) in the serum was observed.

The results are shown in Table 12. In Table 12, the values of serum cholesterol (mean value of 550 mg/dl), of serum phospholipid (mean value of 320 mg/dl) and of serum beta-lipoprotein (mean value of 2500 mg/kg) before administration were respectively subtracted from the respective values after 3 and 6 hours of the administration, and only the differences are shown, respectively. Therefore, the minus value shows the decrease and the plus value shows the increase of the respective values due to the administration. As is clearly seen in Table 12, every active ingredient exhibited an activity of reducing the lipid components of serum as compared to control.

TABLE 12

| | | Activity of reducing blood lipids | | | | | |
|---|---|---|---|---|---|---|---|
| | | Phospholipid (mg/dl) | | beta-Lipoprotein (mg/dl) | | Cholesterol (mg/dl) | |
| Compound | Dose (mg/kg) | 3 hr. | 6 hr. | 3 hr. | 6 hr. | 3 hr. | 6 hr. |
| Sodium p-aminobenzoate-N-D-mannoside | 30 | −37 | −43 | −133 | −142 | −190 | −80 |
| | 300 | −50 | −75 | −156 | −183 | −150 | −234 |
| Sodium p-aminobenzoate-N-D-glucoside | 30 | −25 | −28 | −115 | −147 | −52 | −50 |
| | 300 | −31 | −40 | −127 | −180 | −55 | −60 |
| Sodium p-aminobenzoate-N-D-galactoside | 30 | −28 | −34 | −166 | −142 | −120 | −95 |
| | 300 | −38 | −47 | −321 | −182 | −250 | −240 |
| Sodium p-aminobenzoate-N-L-arabinoside | 30 | −30 | −37 | −89 | −71 | −48 | −48 |
| | 300 | −26 | −51 | −168 | −195 | −77 | −78 |
| Control | — | 0 | −19 | 0 | +3 | +8 | −4 |

Now, the formulation of the active ingredients to make the pharmaceutical composition of the present invention is described below.

In the case where the pharmaceutical composition is used as an antiinflammatory agent, it is able to use the pharmaceutical composition in the form which is convenient to obtain the effectiveness according to the kinds and the symptoms of the disease, and moreover, the active ingredient may be used as itself or may be used as mixtures combined with any diluent allowable in pharmaceutical process and with other medicines.

The pharmaceutical composition of the present invention is administered orally or parenterally and accordingly, the pharmaceutical composition of the present invention may take any form optionally for the oral or parental administration.

The pharmaceutical composition of the present invention may be offered as a form of unit administration. The form of the pharmaceutical composition of the present invention may be powder, granule, tablet, sugar-coated tablet, capsulated one, suppository, suspension, solution, emulsifiable concentrate, ampouled one, injection, etc. As a diluent, any one of solids, liquids and semisolids may be utilized, for instance, excipients, binders, wetting agents, disintegrating agents, surfactants, demulcents, dispersing agents, buffering agents, perfumes, preservatives, dissolution aids and solvents.

Moreover, one or more than one of these adjuvants may be used in combination or in mixtures.

The pharmaceutical composition of the present invention may be formulated by any method, and the amount of the active ingredient contained in the composition (preparation) is generally from 0.01% to 100% by weight.

The pharmaceutical composition of the present invention may be administered orally or parenterally to humans or animals, however, it is preferably administered orally. Sublingual administration is included in oral administration. Parenteral administration includes subcutaneous-, intramuscular- and intravenous injection and the injection by drop method.

The dose of the pharmaceutical composition of the present invention depends upon the age, the personal difference and the state of disease, and whether the object is human or animal and accordingly, an extraordinal amount may be administered than the following dose: Generally, for human, the oral dose is 0.1–1000 mg/kg body weight/day, preferably 1–500 mg/kg/day and the parenteral dose is 0.01–200,mg/kg/day, preferably 0.1–100 mg/kg/day divided into 1–4 parts, one part being administered in one time.

The followings are the more detailed explanation of the formulation and the production of the pharmaceutical composition of the present invention in examples.

EXAMPLE 1 (FORMULATION)

10 parts by weight of one of the active ingredients of the present invention (Sodium p-aminobenzoate-N-L-arabinoside), 15 parts by weight of (heavy) magnesium oxide and 75 parts by weight of lactose were uniformly fixed and formulated into powder or granules. The powder is filled in capsules to be capsulated formulation.

EXAMPLE 2 (FORMULATION)

45 parts by weight of one of the active ingredients of the present invention (Sodium p-aminobenzoate-N-D-galactoside), 16 parts by weight of lactose, 21 parts by weight of crystalline cellulose, 3 parts by weight of polyvinyl alcohol and 30 parts by weight of water were uniformly mixed, crushed and formulated, and then dried and shifted to be granules.

EXAMPLE 3 (FORMULATION)

Granules were prepared as in Example 2, except using sodium p-aminobenzoate-N-D-glucoside instead of sodium p-amino- benzoate-N-D-galactoside, and the mixture of 96 parts by weight of this granule and 4 parts by weight of calcium stearate was compression-formulated to be tablets 10 mm in diameter.

EXAMPLE 4 (FORMULATION)

94 parts by weight of one of the active ingredients of the present invention (sodium p-aminobenzoate-N-L-glucoside), 6 parts by weight of polyvinyl alcohol and 30 parts by weight of water were mixed and the mixture was processed as in Example 2 to be granules. To 90 parts by weight of the thus processed granules 10 parts by weight of crystalline cellulose were mixed and the mixture was compression-formulated to be tablets 8 mm in diameter. The tablets were coated with syrup, gelatine and precipitated calcium carbonate to be coated tablets.

EXAMPLE 5 (FORMULATION)

0.6 part by weight of one of the active ingredients of the present invention (sodium p-aminobenzoate-N-D-galactoside), 2.4 parts by weight of an non-ionic surfactant and 97 parts by weight of physiological saline solution were mixed under heating and then the mixture was sterilized to be an injection. EXAMPLE 6 (Production of p-aminobenzoic acid-N-L-arabionoside and its sodium salt)

A mixture of 4.6 g of p-aminobenzoic acid, 5.0 g of L-arabinoseand 0.5 g of ammonium chloride was heated in 40 ml of 94% ethanol under a reflux condenser. After the reaction was over, crystals separated out when the reaction mixture was kept in a refrigerator. The crystals thus obtained by filtering were washed with ether. The crystals repeatedly recrystallized from 50% methanol were colorless needles. Yield was 45.8%. In the case where ammonium sulfate was used for ammonium chloride, a similar result was obtained.

Thus obtained p-aminobenzoic acid-N-L-arabinoside was dissolved gradually into an aqueous 1% sodium hydroxide solution containing in total the amount of calculated sodium hydroxide and after filtering, the solution was condensed under reduced pressure. The crystals which separated out by the addition of a large excess of acetone to the condensate was dehydrated and dried. Colorless crystals of sodium salt was obtained at the yield of 100%. The total yield from anthranilic acid was 45.8%.

EXAMPLE 7 (production of p-aminobenzoic acid-N-D-glucose and its sodium salt)

A mixture of 5g of p-aminobenzoic acid, 6.4 g of D-glucose and 0.5 g of ammonium chloride was heated in 50 ml of 94% ethanol under a reflux condenser. After the reaction was over, the reaction mixture was condensed to about one third in volume and left in a cool place for a night to be a gel. After adding a small amount of water to the gel, and heating the mixture to obtain a solution, the solution was left in a refrigerator to separate crystals. After collecting the crystals by filtration and washing the thus separated crystals with water, dilute ethanol and then with a small amount of ether, the crystals were recrystallized from 50% methanol as colorless needles. The yield was 33.7%. In the case where ammonium sulfate was used for ammonium chloride in the above-mentioned reaction, a similar result was obtained.

By dissolving thus obtained crystals slowly into an aqueous 1% sodium hydroxide solution in stoichiometric proportions, and filtering the solution then condensing the filtrate and at last adding a large excess of acetone into the condensate, crystals separated out from the acetonic solution. After dehydration and drying, colorless crystals were obtained at the yield of 100% of the p-aminobenzoic acid-N-D-glucoside. Total yield from p-aminobenzoic acid was 33.7%.

EXAMPLE 8 (Production of p-aminobenzoic acid-N-D-galactoside and

A mixture of 1.5g of p-aminobenzoic acid, 2.0 g of D-galactose and 0.1 g of ammonium chloride was heated under a reflux condenser in 30 ml of 94% ethanol. After the reaction was over, the reactant was condensed under reduced pressure and left at a cool place to separate crystals. After filtration of the reactant and washing the collected crystals with water, dilute ethanol and then with a small amount of ether and further recrystallizing from methanol, colorless needle-like crystals were obtained at the yield of 18.1%.

Thus obtained crystals of p-aminobenzoic acid-N-D-galactoside were dissolved in an aqueous sodium hydroxide solution in stoichiometric proportions, and after filtration of the solution, and condensation of the filtrate under reduced pressure, a large excess of acetone was added to the condensate. The thus separated crystals were dehydrated and dried. Colorless crystals were obtained at the yield of 100% based on the p-aminobenzoic acid-N-D-galactoside and at the total yield of 18.1%.

EXAMPLE 9 (Production of p-aminobenzoic acid-N-D-mannoside and its sodium salt)

A mixture of 2.0 g of p-aminobenzoic acid, 3.0 g of D-mannose and 0.2 g of ammonium chloride was heated in 10 ml of ethanol for about one hour under a reflux condenser. After the reaction was over, the reactant was left at room temperature to separate crystals. After filtering the reactant and washing the collected crystals with water, dilute ethanol and then with a small amount of ether, the crystals were recrystallized from 50% methanol to form colorless needles at the yield of 56.1%.

Thus obtained p-aminobenzoic acid-N-D-mannoside was slowly dissolved in a solution forded by dissolving 2.5 mg of sodium hydroxide into 2.5 ml of water. After filtering the solution and condensing the filtrate, a large excess of acetone was added to the condensate Lo obtain crystals. After dehydrating and drying the crystals, they were recrystallized from a mixed solvent consisting of 5 parts by volume of water and 1 part by volume of acetone to obtain colorless crystals of sodium p-aminobenzoate-N-D-mannoside at a yield of 95%, total yield from p-aminobenzoic acid being 95%.

EXAMPLE 10

A case of sarcoma in gastric smooth muscle of a woman of 72. (weight: 47kg)

After having a gastrectomy according to sarcoma in the gastric smooth muscles, the patient had a chemotherapy. After that, the internal taking of 300 mg/day of sodium p-aminobehzoate-N-D-glucoside was commenced. Because of his favorable progress, he left the hospital and became an outpatient. Now, he shows no symptoms without sings of recurrence at all.

EXAMPLE 11

A case of esophageal cancer (squamous epithelial cancer) of a man of 66. (weight: 55kg)

After recognizing a feeling of stricture in forechest on swallowing and imtumescent of a limph node in left supraclavicular fossa, he had a radiation therapy. However, the state was not improved with the limph node in the upper axial grown to thumb-size and on roentgenography a shadow loss of 6 cm in diameter accompanied with cancerous ulcer was found in the upper, middle and lower esophagus with irregularity of its wall. In consideration of his age, the oral administration of 300 mg/day of p-aminobenzoic acid-N-D-glucoside was commenced. Then, the cancerous ulcer of the esophagus was improved to be a irregularity of the mucosa when examined by roentogenography and endoscopy and no malignant tumour was recognized by biopsy. Since then he is an outpatient and his progress is favorable. In addition, the lymph node in the left supraclavicular fossa was reduced to a size of a soybean and there is no tendency of enlarging at all.

EXAMPLE 12

A malignant tumour (Hodgkin's disease) of a man of 65. (weight: 60 kg)

After dehospitalization with safe remission, the intumescence of lymph nodes in left neck and left axial were recognized and he had an introduction of re-remission accompanied with the continuous internal administration of 300 mg/day of p-aminobenzoic acid-N-D-galactoside. The same internal administration is continued until now. The general situation of this patient is favorable with the number of peripheral lymphocytes maintained, and there are no sign of recurrence recognized at all.

EXAMPLE 13

A case of stomach cancer and cancerous peritonitis (carcinoma simplex) of a woman of 60. (weight: 43 kg)

The patient was examined complaining pain in the cardiac space and feeling of abdominal inflation. Gastroroentgenography recognized the stomach cancer of type III - B and an intense stagnancy of ascites. Metastasis to a lymph node in left supraclaviolar fossa was also recognized. According to the patient's desire he became an outpatient and had an internal administration of 300 mg/day of sodium p-aminobenzoate-N-D-mannoside. From after about one month of administration, a size-reduction of the lymph node in the left supraclaviolar fossa from tip of thumb - size to a soya-bean size, however, no remarkable change was found by gastroroentgenography as well as the increase of ascites. Although he was judged to be "improved", he died due to the aggravation

EXAMPLE 14

A case of lung cancer (adenocarcinoma) of a woman of 62. (weight 48 kg)

After living more than 10 years of her operation on the recurrent mammary cancer, she was hospitalized according to the indication of a shadow of mass of 3 cm×2 cm in size in right intermediate lung field at a mass-examination. After irradiation of $^{60}Co$, she had an internal administration of 300 mg/day of sodium p-aminobenzoate-N-D-arabinoside without any side effects. Various examination found no remarkable changes. After one month of taking to the above-mentioned drug, the shadow of mass was reduced in size of 2cm×1.5cm and after 2 months the shadow almost disappeared on examination by roentgenography.

EXAMPLE 15

A case of recurrent cervical cancer (undifferentiated type of squamous epithelial carcinoma) of a woman of 62. (weight: 43 kg)

She was hospitalized with a diagnosis of Stage IIIb of cervical cancer. She left hospital after improvement by Linac external irradiation and intravaginal irradiation of $^{137}Cs$ However, she had a rectal hemorrhage without any effect of internal medical treatments, and had an operation of making artificial anus. After 2 months of the operation, a topical recurrence of the cancer was recognized. Because of the loss of adaptation to the radiation treatment, an administration of 300 mg/day of p-aminobenzoic acid-N-L-arabinoside was commenced. After taking the drug for one month, the progress of the topical recurrence became favorable and the administration is continued until now. Although at the time of recurrence, her body weight showed a remarkable reduction and her general malaisefelling and loss of appetite were very severe, since the beginning of the internal taking of the drug a gradual improvement of appetite was seen without any pain in visiting the hospital. After half a year of internal taking, her body weight showed a gain. Now, no recurrence nor metastasis is found on her.

What is claimed is:

1. A pharmaceutical composition for parenteral administration in dosage unit form comprising 0.1 to 100 mg/kg body weight/day of p-aminobenzoic acid-N-D-mannoside, or a pharmaceutically acceptable salt thereof, effective for the treatment of tumor, and a pharmaceutically acceptable carrier.

2. A pharmaceutical composition for oral administration in dosage unit form comprising 1 to 500 mg/kg body weight/day of p-aminobenzoic acid-N-D-mannoside, or a pharmaceutically acceptable salt thereof, effective for the treatment of tumor, and a pharmaceutically acceptable carrier.

3. The pharmaceutical composition according to claim 1 wherein said pharmaceutically acceptable salt of said p-aminobenzoic acid-N-D-mannoside is sodium p-aminobenzoic-N-D-mannoside.

4. The pharmaceutical composition according to claim 2 wherein said pharmaceutically acceptable salt of said p-aminobenzoic acid-N-D-mannoside is sodium p-aminobenzoate-N-D-mannoside.

5. The pharmaceutical composition of claim 2, in tablet form.

6. The pharmaceutical composition of claim 2, in powder form.

7. The pharmaceutical composition of claim 2, in capsule form.

* * * * *

UNITED STATES PATENT AND TRADEMARK OFFICE
CERTIFICATE OF CORRECTION

PATENT NO. : 4,957,906
DATED : September 18, 1990
INVENTOR(S) : Chikao YOSHIKUMI et al.

It is certified that error appears in the above-identified patent and that said Letters Patent is hereby corrected as shown below:

Title page, after "[*]Notice", correct the Terminal Disclaimer information as follows:

Change "Apr. 19, 2000" to --Feb. 2, 1999--.

Signed and Sealed this

Twenty-fourth Day of August, 1993

*Attest:*

BRUCE LEHMAN

*Attesting Officer*     *Commissioner of Patents and Trademarks*